United States Patent [19]
Davies

[11] Patent Number: 6,156,329
[45] Date of Patent: *Dec. 5, 2000

[54] STRIPPED SPENT SILVER CATALYSTS AND NOVEL USES THEREOF

[75] Inventor: Ronald F. Davies, Queensbury, N.Y.

[73] Assignee: Ames Goldsmith Corporation, Glen Falls, N.Y.

[*] Notice: This patent is subject to a terminal disclaimer.

[21] Appl. No.: 09/211,377

[22] Filed: Dec. 14, 1998

Related U.S. Application Data

[63] Continuation-in-part of application No. 08/735,003, Oct. 22, 1996, Pat. No. 5,849,319.
[60] Provisional application No. 60/006,074, Oct. 24, 1995, abandoned.
[51] Int. Cl.[7] .................................................. A01N 25/08
[52] U.S. Cl. ......................... 424/406; 424/405; 424/408; 424/409; 424/411; 424/413; 424/414; 424/421; 424/618; 424/76.9; 422/28
[58] Field of Search .................................. 424/405, 406, 424/408–415, 421, 76.5, 76.8, 76.9, 618; 106/15.05, 162.1, 606, 611–613, 622, 631–633, 668–670, 692–698, 705–711, 713–722, 739; 252/186.1; 422/28–37; 428/541; 427/419.1; 523/122

[56] References Cited

U.S. PATENT DOCUMENTS

| | | | |
|---|---|---|---|
| 4,608,247 | 8/1986 | Heinig | 424/16 |
| 5,413,789 | 5/1995 | Hagiwara et al. | 424/409 |
| 5,849,319 | 12/1998 | Davies | 424/409 |
| 5,961,843 | 10/1999 | Hayakawa et al. | 210/748 |

*Primary Examiner*—Neil S. Levy
*Attorney, Agent, or Firm*—Howard M. Ellis; Marianne Fuierer

[57] ABSTRACT

Spent silver catalysts, from which the recoverable silver has already been stripped, was discovered to be useful for controlling microorganisms such as bacteria and fungi, including microorganisms in fluids such as water, or on surfaces to which coatings containing the stripped, spent silver catalysts are applied, and also in and on products or substrates in which the stripped, spent silver catalysts are incorporated.

20 Claims, No Drawings

STRIPPED SPENT SILVER CATALYSTS AND NOVEL USES THEREOF

CROSS REFERENCE TO RELATED APPLICATION

This application is a continuation-in-part of application U.S. Ser. No. 08/735,003, filed on Oct. 22, 1996 now U.S. Pat. No. 5,849,319 which claims the benefit of U.S. Provisional application No. 60/006,074, filed Oct. 24, 1995, abandoned.

TECHNICAL FIELD

This invention generally relates to novel uses for the residue from spent silver based catalysts deposited on inert carriers which have been treated for reclaiming their silver values. More particularly, this invention relates to the discovery that this catalytic residue from silver stripping operations can be used alone or as an additive in manufactured products as broad spectrum biocides for controlling microorganisms, especially bacterial and fungal agents of disease.

BACKGROUND OF THE INVENTION

Silver shares Group 1B of the Period Table with gold, platinum and mercury and belongs to the family of noble metals. Silver has also been included in the group of metals referred to as precious metals, a distinction it shares with gold, platinum and palladium. Silver and its compounds are used in many fields, the most prominent of which are probably coinage and photography. However, silver and its compounds have a number of other uses as well.

Silver, for instance, is employed as a catalyst in several important chemical processes. For example, silver is utilized as a catalyst in the oxidation of ethylene to ethylene oxide. About 9.6 million metric tons of ethylene oxide were produced in 1992, a large increase over the 3.3 million tons produced in 1988, and the demand for ethylene oxide continues to grow.

Silver catalysts generally include three or four components. These components include a support material, the catalytically active silver, a promoter, and optionally, an inhibitor. Silver catalysts and specific components thereof are often proprietary.

Silver catalysts are generally supported. In the case of the catalysts used in the oxidation of ethylene to ethylene oxide, the support is a solid, inert material, capable of near continuous exposure to a temperature of about 250° C. to 300° C. in the presence of ethylene, air or oxygen, and ethylene oxide, as well as trace amounts of contaminants. Typical support materials include alumina, aluminosilicate and silicon carbide ceramics, zeolites, glass, and quartz. The support material is available in various, generally extruded shapes such as pellets, rings, grain, and so forth.

Catalytically active silver can be prepared by treating an aqueous silver salt solution with alkali; by thermal decomposition of silver salts, particularly silver carbonate, oxalate, or another silver salt of an organic acid; by reducing a silver salt with hydrogen, formaldehyde, hydrazine, or hydroxylamine; by the electrolysis of a solution of a silver salt; or by selectively removing secondary metals from a silver alloy.

The promoter in silver catalysts increases the activity and selectivity while enhancing the longevity of the catalyst. The promoters are generally salts of alkali or alkaline earth metals, such as cesium, rubidium, potassium, calcium, or barium.

An inhibitor, or anti-catalyst, is sometimes present to suppress further oxidation of the ethylene oxide to carbon dioxide and water. Inhibitors present in the silver catalyst are generally alkali metal halides or cyanides. Alternatively, the inhibitor can be added to the vapor phase in which the oxidation takes place. Ethylene dichloride, ethylene dibromide, other alkyl halides, aromatic hydrocarbons, amines, and organometallic compounds can be used in this way.

The catalytically active silver, in combination with the promoter and the inhibitor, if present, are applied to the support material by coating the support with a suspension of these components in a fluid, by impregnating a porous support with the suspension, or by some functionally equivalent technique. The catalytically active silver generally comprises about 10–20 percent by weight of the finished silver catalyst.

In the catalytic oxidation of ethylene, the surface of the silver is thought to be covered with oxygen, and the catalyst may more properly be described as a silver oxide, rather than metallic silver. The understanding of the nature of the catalytic sites, the mechanisms by which the promoters and the inhibitors are effective, etc. is not complete, but such understanding is not required for the catalysts to be effective. Indeed, the methods can be practiced successfully regardless of the exact nature of the silver catalyst and the mechanism by which it functioned as a catalyst.

The aforesaid description illustrates the makeup of a silver catalyst employed in the production of one representative product, ethylene oxide, from one representative feedstock, i.e., ethylene. Silver catalysts employed in processes for taking other reactants to other products are similar but not identical to the silver catalysts described above. However, all such catalysts after being stripped of removable silver are regarded as being useful in the methods of the present invention.

The life expectancy of the silver catalysts employed in the oxidation of ethylene to ethylene oxide typically is about 1–2 years. Factors which are known to affect the useful life of catalysts are the rate of ethylene feed over the catalyst and possible exposure of the catalyst to poisons, such as sulfur. Thus, the silver catalyst employed in the oxidation of ethylene must be replaced periodically. The same fate awaits similar silver catalysts employed in other processes.

It is generally possible to strip and recover the silver values from spent silver catalysts and recycle them. This stripping operation is typically accomplished by extracting or leaching the spent catalyst with an acid in which the silver is soluble, such as nitric acid, and then thoroughly washing the catalyst. The liberated silver metal can be recovered from aqueous solutions by methods well known to those skilled in the art.

Heretofore, after the silver was recovered, the residue, which was mostly the support material was usually discarded with the belief that the material was depleted of value and/or utility. Although some of the stripped, spent silver catalyst was incorporated into refractories and abrasives, these outlets consumed only a small fraction of the 5 million pounds of stripped, spent silver catalyst currently generated each year from the oxidation of ethylene alone. In this regard, tons of stripped spent silver catalyst are discarded in landfills every year.

Since the stripped, spent silver catalysts are not biodegradable, the cost of land filling the material is quite high especially in light of the fact that land filling causes environmental concerns and potential liabilities to the landfill operator, as well as to the disposer. Thus, new beneficial uses for stripped, spent silver catalysts are needed thereby reducing waste management concerns and utilizing any potential value remaining in the material.

SUMMARY OF THE INVENTION

For purposes of this invention, the terms and expressions below, appearing in the specification and claims, are intended to have the following meanings:

"Stripped, spent silver catalyst" refers to the residue from supported silver catalysts described above from which the recoverable silver values have been removed.

"Microorganism" as used herein refers mainly to self-replicating microorganisms, which include bacteria, fungi and especially the infectious agents of disease which pose a threat in a biological system.

"Control" means to decrease the concentration of the microorganisms, typically bacteria, fungi and possibly certain viruses by killing, degrading or preventing their reproduction.

Accordingly, it is the primary objective of this invention to provide a new use for stripped, spent silver catalysts which takes advantage of a previously unutilized and unrecognized useful characteristic, and therefore, unappreciated property of these materials. That is to say, this inventor, to the best of his knowledge, was the first to recognize and appreciate the presence of silver values remaining in stripped spent silver catalysts in sufficient concentration to impart a utility which is dependent on the presence of mere trace amounts of one component, namely silver, of the original multi-component catalytic composition of matter. As previously mentioned, heretofore stripped, spent silver catalysts were used as refractory and abrasive materials, or alternatively, disposed of as landfill. Thus, this invention provides for novel and inventive new uses for stripped, spent silver catalysts in methods for controlling microorganisms by contacting them with a biocidally effective amount of the stripped, spent silver catalyst. Since bulk quantities of stripped, spent silver catalysts are usually discarded, the methods of this invention have the advantage of a very economical means for controlling microorganisms while simultaneously reducing the environmental problems normally associated with the disposal (storage) of such materials.

It is a further objective of this invention to provide an inexpensive means for controlling potentially harmful microorganisms, e.g., bacteria, fungi, and so on, which may be present, for example, in fluids, such as the drinking water of a municipality, or water of uncertain purity in a remote location. The stripped, spent silver catalysts can be employed as broad spectrum biocides in swimming pools, hot tubs and other recreational bodies of water or in other aqueous-containing systems, such as aquariums. Representative examples of an aqueous system would include the decontamination of recirculating water in cooling towers or condensate from larger air conditioning systems. The methods are also applicable to the sterilization of effluents from sewage treatment facilities, including sludge, and contaminated effluents from manufacturing plants.

It is further envisioned by this inventor to utilize the stripped, spent silver catalysts as surface fill in sanitary septic systems thereby reducing possible bacterial contamination of surrounding areas after heavy rains or flooding of the septic system. Moreover, the stripped, spent silver catalyst may be used as fill in septic pools or ponds that have become acidified or alkaline due to high bacteria levels.

It is an additional object of this invention to provide a method for protecting the surfaces of various articles against the growth of microorganisms by incorporating stripped, spent silver catalysts into coatings for applying on said surfaces. The stripped, spent silver catalyst may be incorporated into emulsions, such as paints, for applying to surfaces in a damp environment thereby reducing the growth of mildew and/or mold due to fungal activity.

It is yet another objective of the present invention to extend the longevity of various products by incorporating stripped, spent silver catalyst therein. For instance, The stripped, spent silver catalyst may be added to composite substrates and manufactured products such as grout, cement, cement blocks, patio brick, composite wood products, and asphalt roofing material thereby extending the life of the product by reducing microbial activity therein.

Additionally, it is an object of the present invention to provide absorbent material comprising stripped, spent silver catalysts to be used in animal husbandry for absorbing animal waste products thereby reducing odors and providing a more sanitary environment.

A still further object of the present invention is to incorporate a sufficient amount of stripped, spent silver catalyst in a composite manufactured product to substantially reduce the growth of microorganisms by the slow release of silver over an extended period of time and use without the need of mechanical abrasion of the catalyst substrate to release the silver.

DETAILED DESCRIPTION OF THE INVENTION

This invention provides a method for controlling microorganisms which comprises contacting the microorganisms (or medium containing the microorganism) with a biocidally effective amount of a stripped, spent silver catalyst.

The amount of stripped, spent silver catalyst which is a biocidally effective amount will vary depending upon a number of factors. The amount of silver depends upon the chemical composition of a stripped, spent silver catalyst, the manufacturer of the original catalyst and finally the specific chemical process in which the recoverable silver was leached from the support material. Some extraction processes are more aggressive and achieve a greater recovery of the recyclable silver thereby providing a support material wherein any remaining silver is well attached to the support material, e.g., by adsorption or intercalated into the matrix of the catalyst.

Accordingly, it has been determined that the degree of biocidal activity of a stripped, spent silver catalyst is related to the amount of silver contained therein as the examples which follow show.

This inventor found that although substantially all of the silver values from the spent catalyst are removed in the stripping process, typically a trace amount, usually from about 0.04 to about 0.1 percent by-weight, of silver remains in this residue, e.g., on the order of about 50–900 ppm of silver. However, depending on the method of stripping and the harshness of the leaching process the silver content can increase from about 0.1 to about 0.25 percent by weight of silver. Consequently, the biocidally effective amount of stripped, spent silver catalyst will depend upon the silver content of the catalyst, a lesser amount of the stripped, spent silver catalyst being required to control a given concentration of microorganisms if the silver content is at the higher end of the range.

In addition, the amount of stripped, spent silver catalyst which is a biocidally effective amount will depend upon the length of time during which the microorganisms and the strippable, spent silver catalyst are in contact, a longer contact time requiring less of the stripped, spent silver catalyst. Also, some microorganisms are easier to control than are other microorganisms, so the biocidally effective amount will be less to control a susceptible microorganism than a resistant microorganism.

As indicated above, and as will be further discussed below, in a typical stripped, spent silver catalyst, the alumina or other types of support material predominate, and this support material can be crushed and screened to produce a grain or powder of the particle size desired for the application at hand. The stripped, spent silver catalyst can be used either alone or introduced into other substances to control the growth of microorganisms thereby providing beneficial effects, such as preventing damage to a composite substrate and/or increasing the useful life of same.

One of the benefits of using the stripped, spent silver catalyst of the present invention is that mechanical manipulation or abrasion of the support material is not required for the silver to be released and effective. Thus, stripped, spent silver catalyst may be added to substances that remain in a static state and yet the microbial benefits of the catalyst material are still manifested. For instance, applying a surface coating to basement walls, whether concrete blocks, cement or some type of particle composite board, is a preferred method to enhance the look of the wall. However, most paint formulations do not prevent the growth of mildew and mold. As such, the inclusion of stripped, spent silver catalyst in a paint formulation will control fungal growth and protect the surface from discoloration due to microbial activity that may occur in a damp basement.

In formulating a paint medium, the stripped, spent silver catalyst may be crushed and screened to a particle size resembling pigment materials, such as titanium dioxide, and used as an extender. In this regard, the support material can fulfill two requirements, namely acting as an extender which increases the covering and weathering of the paint, and also controlling unwanted microbial growth on the protected surface. The silver content in the stripped, spent silver catalyst should be evenly dispersed through the paint formulation thereby providing an essentially homogeneous medium that will inhibit growth of unwanted microorganisms contacting the coating. It is within the methods of the present invention to incorporate a sufficient amount of the stripped, spent silver catalyst into surface protective coatings, such as oil based paints and latex-based paints to reduce the growth of mold and/or mildew on a coated surface. Preferably, the stripped spent silver catalyst is added in an amount from about 1 to about 25 percent by weight of the paint constituents, and more preferably, from about 5 to about 15 percent by weight.

It is also envisioned by this inventor to include the stripped, spent silver catalyst material into marine paint thereby providing a protective coating for boats, docks, and other surfaces exposed to damp, moist environments.

The methods of the present invention include adding stripped, spent silver catalyst to construction materials such as cement, concrete blocks, bricks, cellulose roofing underlayment, asphalt roofing shingles, gypsum board, drywall cement, tile grout, pressed board, masonite, gypsum board, chip board, and numerous other construction materials that are attacked by microorganisms resulting in deterioration of the construction material.

For instance, stripped, spent silver catalyst may be included in several roofing system components to extend the life of a roof system. The life span of a roof is approximately twenty years and one of the factors reducing this life span is attack of the roof material by microorganisms. Roofing paper underlayment is currently manufactured with cellulose materials. In the right environment this organic cellulose material can become a breeding ground for microorganisms. Fungal activity occurs on the paper underlayment and moves to the surface of the asphalt shingles causing an unsightly mold with a concomitant deterioration of the surface. Accordingly, a sufficient amount of the stripped, silver spent catalyst can be crushed and pulverized to dust particle size and added to the cellulose material to control the growth of microorganisms while still maintaining the proper surface, opacity, strength and feel of the paper underlayment. The stripped, spent silver catalyst may act as a filler in the paper and occupy the spaces between the fibers of the cellulose material. Fillers are usually inorganic substances, therefore, the stripped, spent silver catalyst can perform dual functions, that being, a filler and resisting microbial growth. Preferably, about 1 percent to about 20 percent by weight of catalyst is added to a pulp formulation depending on the overall silver content remaining in the stripped, spent silver catalyst.

As a second line of defense to prevent the spread of fungal activity, a biocidally effective amount of the stripped, spent silver catalyst may be added to asphalt shingles. Asphalt shingles comprise an impregnated asphalt felt with a harder coating of asphalt on the weather side of the shingle which is coated with granules either in natural of artificial colors. In the past, the felt was composed of felted fibers of selected rags, but currently, newspaper and waste paper products are used in place of fabrics. The increase of cellulose materials in the roofing felt has provided an environment for microorganisms to thrive. Accordingly, the inclusion of the stripped, spent silver catalyst will control the growth of microorganisms. Depending on the particle size, the catalyst support material can be introduced in both the felt product and used to augment the granules on the weather surface of the shingles.

The stripped, spent silver catalyst may be included in cementeous masonry products which upon curing will be structurally supportive with antimicrobial activity on the hardened surfaces. The methods of the present invention include adding a biocidally effective amount of the stripped, spent silver catalyst to a liquid formulation that upon hardening and setting comprises grout, concrete masonry blocks, bricks including cement or clay, and mortar. Stripped, spent silver catalyst may be added to the cement products named above thereby providing antimicrobial action that slowly releases from the products. Generally, cement is composed of silica, alumina, calcium oxide and several other oxides in minimum quantities. As such, stripped spent silver catalysts may replace or augment the alumina component. Preferably, about 5 to about 10 percent of the stripped, spent silver catalyst may be added to the other components of cement thereby providing a biocidally effective amount of silver to products manufactured with cementeous material.

In the process of manufacturing concrete or concrete blocks, the aggregate used for mixing with cement may include stripped, spent silver catalyst replacing some of the aggregate in an amount usually used in formulating concrete and well known in the art. The stripped, spent silver catalyst should be added in a sufficient amount to control microorganisms but not hinder the hydration and hydrolysis processes involved in setting and hardening of the cement.

Wood products may also be impregnated with antimicrobial activity provided by inclusion of stripped, spent silver catalyst. With the increasing price of board foot lumber, there is an emphasis towards using cellulose material that was previously considered waste products and incorporating same into composite wood products. Many products currently available comprise cellulose materials such as wood chips, treebark, cardboard, sawdust and mixtures thereof mixed with an adhesive substance and compressed into a specific shape for a particular application, e.g., pressed board siding, chip board, and masonite. The addition of stripped, spent silver catalyst to the cellulose material provides a wood product that is protected from microbial activity and which may extend the life and appearance of the product. The stripped, spent silver catalyst may be added in a sufficient amount to reduce microbial activity but still provide for a structurally stable composite wood product.

It has been discovered by this inventor that adding the stripped, spent silver catalyst to absorbent materials which are utilized for absorbing animal waste products can control microbial activity thereby reducing odors and extending the time of usability for the product. For example, commerically available "kitty litter" may include about 0.5 to about 1.5 percent by weight of the stripped, spent silver catalyst which extends the acceptable time of using the "kitty litter" before a pet owner needs to replace the absorbent material.

Stripped, spent silver catalyst may also be added to sawdust, zeolites, cellulose materials and other absorbent substrates that are used for maintaining a sanitary environment for raising livestock and/or fowl. Odors associated with animal waste products are usually attributed to bacteria growth and with a reduction in microbial activity there should be a reduction in offensive odors.

Most absorbent materials used for absorbing animal wastes are disposed of in either a sanitary landfill or, if used in animal husbandry, land filled directly on farm property. In the United States, the Environment Protection Agency (EPA) regulates the disposal of silver in landfills and the amount of silver remaining in the material may not exceed 5 ppm. Any product having a greater amount of silver must be considered hazardous waste and disposed of as such. Accordingly, the amount of stripped spent silver catalyst added to "kitty litter" or other absorbent materials used for animal waste products collection must not exceed the current threshold limit of 5 ppm of silver in the material. It should be noted this threshold limit may be raised or completely eliminated in light of the fact that in early 1998 the Federal EPA eliminated regulating silver content in primary drinking water based on the conclusion that silver has "little or no potential for adverse health effects associated with (its) presence in drinking water." (Federal Register, vol. 56, no 20, p. 3597). As such, the amount of stripped, spent silver catalyst incorporated into absorbent material may be increased in the future to provide higher levels of antimicrobial activity.

Stripped, silver catalyst may also be added to aggregate materials, such as sand, pebbles, mineral fragments, rocks and mixtures thereof. During heavy rains and/or poor soil drainage, sanitary septic systems including leach fields can overflow and contaminate the surrounding area with bacteria, e.g., E coli. In this regard, stripped, spent silver catalysts may be mixed with the fill aggregate and used minimally for capping the upper surface of the system thereby acting as a first line of defense in preventing contamination of surrounding areas. The amount of the stripped, spent silver catalyst added to the aggregate will be determine by the silver content remaining in the stripped catalyst materials and the current threshold limitation dictated by EPA regulations.

As stated above, the stripped, spent silver catalyst may be used alone or added as a component to other composite materials. Silver is considered to be non-toxic to humans according to the recent removal of silver from the regulated constituents found in drinking water. As such, silver has been found to aid in water purification as a substitute for chlorine. Purification of water with silver has been found to be effective in reducing bacteria counts without the offensive taste which occurs with the use of chlorine. Accordingly, stripped, spent silver catalyst may be used in a number of steps involved in purification, including water filtration. It may also be utilized in other systems that require storing or recirculating water, e.g., steam purification systems, cooling systems, dehumidifiers, humidifiers and pool filter systems.

Additionally, stripped, spent silver catalyst can be loaded into septic pools that have become acidified or alkaline due to increased bacteria growth. With the addition of stripped, spent silver catalysts in septic pools or ponds, bacteria growth can be inhibited with a concomitant reduction of odors.

The Examples which follow provide a base which is sufficient to provide an estimate of the biocidally effective amount for a given situation, but a certain amount of experimentation may be necessary to optimize the amount of experimentation may be necessary to optimize the amount of stripped, spent silver catalyst to employ in a given situation.

For Examples 1–7, samples of seven stripped, spent silver catalysts were dried, crushed and evaluated for biological activity. The samples had been obtained from a variety of sources and were of unknown composition. Each of the samples was assayed for silver content by the procedure of EPA method SW 846 coupled with EPA method SW 846 7760A, and the samples were found to contain between about 400 and about 900 mg silver per kg as shown in Table 1 below.

The seven samples were evaluated for the their ability to control *E.coli* and *E. faecium* bacteria as follows:

Preparation of the Challenge Microorganisms

*Escherichia coli* (ATTC No. 11229), a gram negative bacterium, was subcultured onto standard plate count agar, and *Enterococcus faecium* (ATTC No. 6569), a gram positive bacterium, was subcultured onto bile exculin azide agar the day before the biocide test. On the test day the cells were harvested by removing the growth from the agar surface using five milliliters of phosphate buffered water. The cells were centrifuged in sterile tubes to remove any media debris and the supernatant was transferred to a sterile container. The cell concentration was determined by the percent light transmission using a Genesys 5 spectrophotometer at 530 nm and compared with the laboratory database. The *E.coli* transmission was adjusted to 88% and the *E. faecium* to 85% to have approximately $2 \times 10^8$ cells per milliliter.

Biocide Test

A cell suspension of ten milliliters of either *E.coli* or *E. faecium*, with a cell density of $2 \times 10^6$ was prepared for each test material. The test material was weighed and added to the cell cultures. The tubes were mixed continuously for 30 minutes. At the end of the incubation time, 0.1 ml of the solution was added to 100 mls of sterile buffered water. From this dilution, 0.1 ml was removed and filtered through a 0.45 micron filter, then the remaining amount (99.9 mls) was filtered through another filter. The filters were put onto the culture media and incubated at 35.0±0.5 degrees C. for 22 to 24 hours. After incubation, the plates were counted and the percent reduction in cell concentration compared with the control.

Inoculum Control

A positive control was used to determine the cell density after the 30 minutes contact time. A post plate, negative control was used to show no cross-contamination and filtered at the end of the experiment.

The test data are shown in Table 1 below.

TABLE 1

Biocidal Screen of Stripped, Spent, Silver Catalyst Samples

| Sample | Grams of Sample (per 1 x $10^7$ cells) | Concentration of Silver mg silver/ kg of material | E. Coli Percent Reduction | E. Faecium Percent Reduction |
|---|---|---|---|---|
| A | 1.0 | 450 | 54.4 | 16.9 |
| B | 1.0 | 600 | 100.0 | 87.3 |
| C | 1.0 | 760 | 100.0 | 99.5 |
| D | 1.0 | 820 | 100.0 | 99.8 |
| E | 1.0 | 510 | 8.0 | 91.0 |
| F | 1.0 | 540 | 58.0 | 88.7 |
| G | 1.0 | 590 | 47.5 | 87.3 |

On the basis of the results in Examples 1–7, it is concluded that each of the seven stripped, spent silver catalysts exhibited the ability to control both gram positive and gram negative bacterial microorganisms.

Specific embodiments of the method of this invention are illustrated in the following Examples:

EXAMPLE 8

Stripped, Spent Silver Catalyst as a Water Treatment

Sterile, deionized water (1.0 liter)in an Erlenmeyer flask is contaminated with E. faecium at the level of $2\times10^6$ microorganisms per milliliter as determined by the spectrophotometric method, monitoring the transmission of the contaminated water at 530 nm, as described above. A 10 ml sample of the contaminated water is set aside. The dried, crushed, stripped, spent catalyst of Example 2 (10 g) is added to the remainder of the contaminated water, and the mixture is stirred for 0.5 hr. at room temperature, at the conclusion of which the mixture is filtered. The filtrate and the untreated, contaminated water previously set aside are cultured as set forth above under "Biocide Test." After incubation, the plates are counted and the differences noted. As a result, it is concluded that treatment of the water with the stripped, spent catalyst reduced the E. faecium content of the water.

EXAMPLE 9

Stripped, Spent Silver Catalyst as a Surface Protectant

A coating is formulated by combining 100 g boiled linseed oil and 50 g of the powdered, stripped, spent catalyst of Example 7. The resulting mixture is milled in a ball mill containing alumina milling media for a period of five days. The mixture is then recovered from the ball mill, and the stripped, spent catalyst remains homogeneously distributed in the linseed oil. A flat glass plate is coated on about one-third of its face with the linseed oil-based mixture, and on another one-third of its face with the pure boiled linseed oil. The coated plate is set aside for two weeks in a small oven maintained at about 80° C. At the end of this period, the coatings have hardened, and the glass plate is removed from the oven.

The glass plate is placed in a large Petri dish, and 25 ml of an aqueous culture containing $2\times10^6$ E. Coli microorganisms per ml is poured onto the coated side of the glass plate, flooding portions of both coatings as well as the uncoated one-third of the surface. The Petri dish is then covered. After being in contact with the surfaces for 30 min, pipettes are employed to transfer and culture 0.1 ml of the liquid from each third of the glass plate as set forth above under "Biocide Test." After incubation, the plates are counted and the differences noted, leading to the observations that the linseed oil coating which contained the stripped, spent silver catalyst inhibited the growth of E. coli, as compared to the uncoated surface, as well as the surface coated with pure linseed oil.

EXAMPLE 10

Stripped, Spent Silver Catalyst as a Paper Additive

A bundle of paper towels is sterilized in a steam sterilizer. Sterile towels are torn into small pieces, added to a flask containing sterile water and stirred vigorously for several hours until a homogeneous pulp containing about 30 percent solids is produced. The wet pulp is divided approximately in half. One portion of the pulp is made into a sheet of paper on a hand screen. To the other half portion of the pulp an amount of the powdered, stripped, spent silver catalyst of Example 4 above sufficient to constitute about 25 percent by weight of the combination of the dry paper plus spent catalyst is added, and a sheet of paper is produced from the mixture on the hand screen.

After drying the two sheets of paper at room temperature for two days under sterile conditions, each sheet is crumpled into a separate Erlenmeyer flask, 200 ml of a culture containing about $2\times10^6$ E. coli microorganisms per ml is added and the mixture, in each case, is allowed to stand for 24 hours. At the conclusion of this period, the supernatant liquid in each flask is cultured as set forth above under "Biocide Test." It is observed that the E. coli level in the culture derived from the flask containing the paper impregnated with the stripped, spent silver catalyst is lower than the E. coli level in the other culture.

Whereas, the method of this invention has been described by reference to the specific Examples set forth above, it is not intended that the invention be limited to those Examples. The invention is to be limited only by reference to the following claims.

That which is claimed is:

1. A method of controlling microorganisms which comprises contacting the microorganisms with a biocidally effective amount of a stripped, spent silver catalyst having a concentration of about 0.1 to about 0.25 percent by weight of silver.

2. A method of controlling microorganisms present in a substance which comprises contacting the microorganisms in the substance with a biocidally effective amount of a stripped, spent silver catalyst having a concentration of about 0.04 to about 0.25 percent by weight of silver.

3. The method according to claim 2 wherein the substance is a fluid.

4. The method according to claim 3 wherein the fluid is water and the microorganisms are contacted with the stripped, spent silver catalyst in a water filtration system comprising the stripped, spent silver catalyst.

5. The method according to claim 2 wherein the substance is a composite substrate.

6. The method according to claim 5 wherein the composite substrate is a cementeous masonry product selected from the group consisting of grout, concrete masonry blocks, cement bricks and mortar.

7. The method according to claim 5 wherein the composite substrate is an absorbent material.

8. The method according to claim 5 wherein the composite substrate is roofing material selected from the group consisting of asphalt shingles, asphalt felt, and roofing underlayment.

9. The method according to claim 7 wherein the absorbent material is used in absorbing animal waste products.

10. The method according to claim 5 wherein the composite substrate is a cellulose material selected from the group consisting of wood chips, cardboard, sawdust, tree bark and mixtures thereof.

11. A method of controlling microorganisms in and on the surface of a substance which comprises introducing a biocidally effective amount of a stripped, spent silver catalyst to the substance, the stripped spent silver catalyst having a concentration of about 0.04 to about 0.25 percent by weight of silver.

12. The method according to claim 11 wherein the substance is a liquid formulation which upon curing forms cementeous masonry products.

13. The method according to claim 11 wherein the substance is a cellulose material selected from the group consisting of paper pulp, sawdust, woodchips, tree bark and mixtures thereof.

14. The method according to claim 11 wherein the substance is an absorbent material.

15. The method according to claim 11 wherein the substance is a roofing material selected from the group consisting of asphalt shingles, asphalt felt, and roofing underlayment.

16. The method according to claim 14 wherein the absorbent material contains about 0.5 to about 1.5 percent of the stripped spent silver catalyst.

17. The method according to claim 11 wherein the substance is an aggregate.

18. The method according to claim 17 wherein the aggregate is a member selected from the group consisting of sand, pebbles, mineral fragments, rocks and mixtures thereof.

19. The method according to claim 11 wherein the substance is contaminated water in a septic pond.

20. The method according to claim 11 wherein the substance is a surface coating medium.

* * * * *